United States Patent [19]

Brown et al.

[11] 4,360,387

[45] Nov. 23, 1982

[54] ISOMORPHOUS JOJOBA OIL COMPOSITIONS CONTAINING TRANS-ISOMERIZED JOJOBA OIL

[75] Inventors: James H. Brown, Chappaqua; Harry Olenberg, Bronx, both of N.Y.

[73] Assignee: Jojoba Growers & Processors Inc., New York, N.Y.

[21] Appl. No.: 241,801

[22] Filed: Mar. 9, 1981

Related U.S. Application Data

[63] Continuation-in-part of Ser. No. 177,971, Aug. 15, 1980, Pat. No. 4,239,298.

[51] Int. Cl.$^3$ .............................................. C09D 3/26
[52] U.S. Cl. .................................... 106/243; 106/270
[58] Field of Search ...................... 106/243, 244, 270; 260/405.6

[56] References Cited

U.S. PATENT DOCUMENTS 2,350,082  5/1944  Taussky ............................ 260/405.6

Primary Examiner—Lorenzo B. Hayes
Attorney, Agent, or Firm—Wolder, Gross & Yavner

[57] ABSTRACT

Useful isomorphous compositions of trans-isomerates of jojoba oil with hydrogenated jojoba oil are described. They are useful as candle waxes, non-stick cooking sprays, cosmetic vehicles, carriers for solid "detergent" soaps, leather treatments, hand modifiers for textiles including both woven and non-woven fabrics. The compositions consist of liquid, solid and semi-solid solutions of the components thereof. They are formed by heating to melting of the components and then cooling the solutions.

5 Claims, 1 Drawing Figure

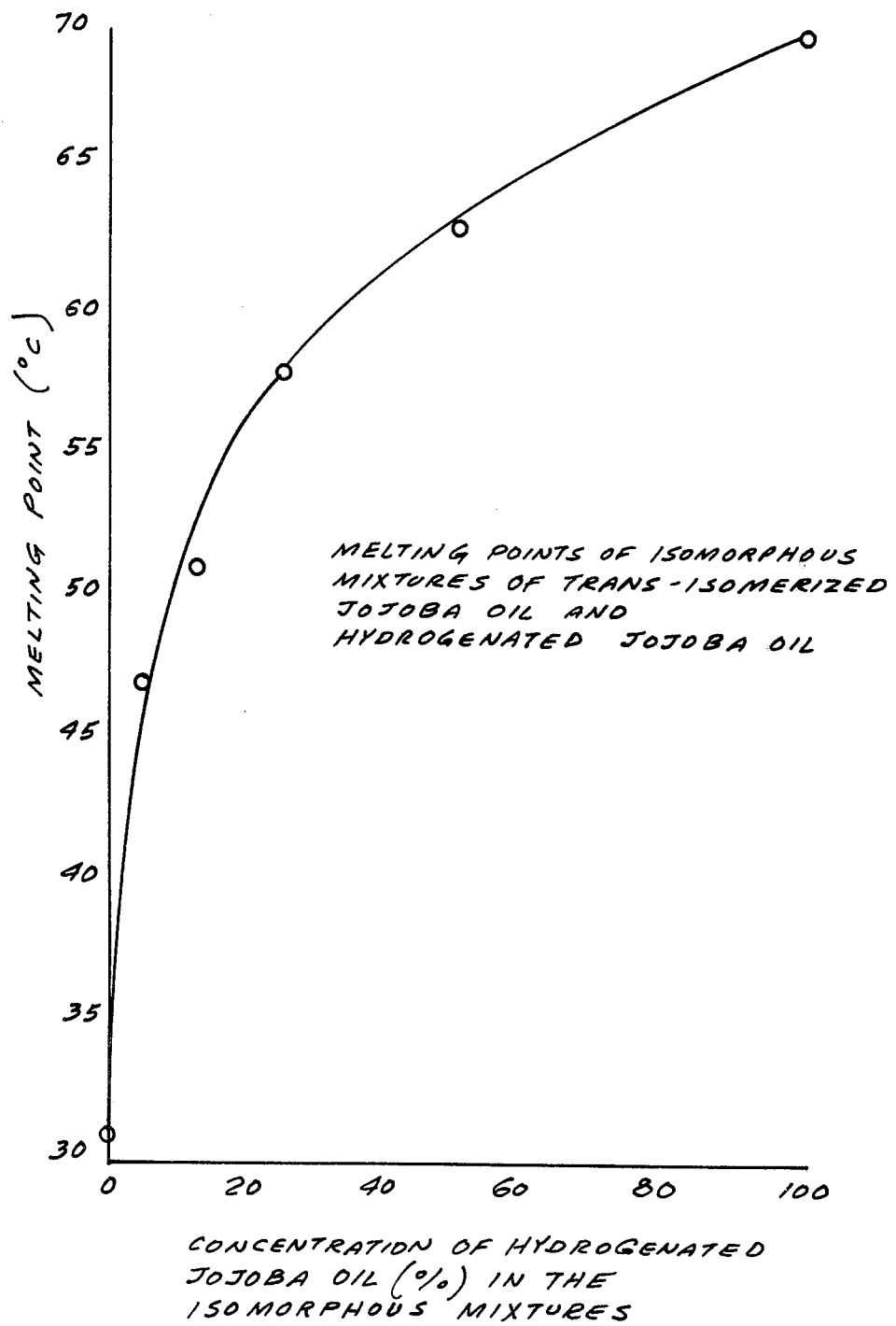

ISOMORPHOUS JOJOBA OIL COMPOSITIONS CONTAINING TRANS-ISOMERIZED JOJOBA OIL

RELATED APPLICATIONS

This application is a continuation-in-part of our allowed U.S. Patent Application Ser. No. 177,971 filed Aug. 15, 1980, now U.S. Pat. No. 4,239,298.

FIELD OF THE INVENTION

This invention relates to novel jojoba oil compositions incorporating isomerates of jojoba oil in combination with hydrogenated jojoba oil. More particularly it relates to useful compositions comprising blends of the trans-isomerates of jojoba oil with hydrogenated jojoba oil to provide candle waxes, food machinery lubricants, non-stock cooking sprays, cosmetic vechicles, semi-solid carriers for solid "detergent soaps", leather and fabric sizes, hand modifiers for woven and non-woven fabrics, and similar compositions utilizing semi-solid and solid wax-like compositions free from glyceryl esters.

BACKGROUND OF THE INVENTION

As set forth in our previous application, Ser. No. 177,971 filed Aug. 15, 1980, jojoba oil is unique among vegetable oils as sperm oil is unique among animal oils in that it is a liquid wax. In contrast to other vegetable oils which are triglyceryl esters; (one mole of glycerol esterified with three moles of long-chain fatty acids), jojoba oil, (as well as sperm oil), is a wax ester, (one mole of a long-chain alcohol esterified with one mole of a long-chain fatty acid. As described in the aforesaid initial application, Ser. No. 177,971 natural jojoba oil has a cis-configuration. By the process of the aforesaid application a controlled isomerization reaction is provided which affords a controlled conversion of the cis-configured oil to the transconfiguration. This isomerization reaction usually is permitted to proceed until cis-trans, isomerized mixtures having the consistency of butter result. These butter-like isomerate mixtures have liquifying points in the range 25°–44° C. and preferably about 27°–35° C. so that they are liquid upon contact with the skin. Mixtures having such melting points are desirable for certain cosmetic vehicles. In fact they may serve as such vehicles. At present an isomerate mixture having a buttery consistency and liquifying at about 31° C. is commercially available.

There is need for solid wax-like materials (in contrast to the semi-solid isomerates) having the useful properties of jojoba oils. Waxes of this type would be particularly useful to replace saturated animal, mineral or vegetable waxes from other sources in the preparation of special solid formulations for food, cosmetic or machine lubricating uses. Attempts have been made to use hydrogenated jojoba oil. Jojoba oil hydrogenate is a white, hard, crystalline material having a m.p. of 68°–70° C. This material, like all high melting waxes, is very brittle at room temperature. Attempts have been made to modify jojoba oil hydrogenate by blending the hydrogenat with jojoba oil. When the oil and the hydrogenate are blended as by melting, the melting points of the resulting cooled compositions can be adjusted to within any desired temperature between the melting points of the two components. However on standing 3–5 days, the cooled compositions become grainy and the jojoba oil bleeds from the compositions, leaving behind the solid hydrogenate. The physical properties of such compositions are thus non-homogeneous and thus undesirable. Similar grainy results are obtained by partially hydrogenating jojoba oils.

THE INVENTION

This invention is based on the discovery of the successful homogeneous compositions of wax-like consistency consisting of an isomorphous system of jojoba oil hydrogenate and the transisomerate of jojoba oil in mutual solid solution. Blends of various proportions of these isomorphous components can be prepared that are stable solids. In addition because of their isomorphous nature, these mixtures do not evidence any eutectic condition but the compositions show increasing melting points with increases in the amount of jojoba hydrogenate in the compositions. Thus the invention provides solid, waxy compositions consisting entirely of jojoba-derived compounds and having useful melting points. They do not separate as they are in homogeneous condition.

The jojoba oil hydrogenate used for the preparation of these compositions is prepared and has the physical properties as described in the 1975 National Academy of Science report entitled: "Products From Jojoba: A Promising New Crop For Arid Lands." Details of the preparation are outlined therein (pg. 20 ff.) and it is now commercialy available. The suggested jojoba oil partial hydrogenates mentioned therein are not the creamy products postulated but rather are grainy mixtures of the cis-oriented liquids and the solid hydrogenate.

The buttery trans-isomerized jojoba oil used for the preparation of the composition of this invention are described and prepared by the isomerization process described in the aforesaid U.S. Patent Application Ser. No. 177,971 filed Aug. 15, 1980, now U.S. Pat. No. 4,239,298. These isomerates have the trans-configuration in contrast to the cis-configuration of the natural jojoba oil. These transisomerates have liquefying points in the range of 25°–44° C. and preferably for the purposes of this invention, liquiefying at about 31°–35° C. These isomerates are preferably prepared by contacting the cis-configured natural jojoba oil with an acidic-clay at temperatures in the range of 150°–350° C. until the desired degree of isomerization is achieved.

DETAILED DESCRIPTION

The compositions of this invention are mutual solid solutions of their components, the isomerates and the hydrogenate. At low melting ranges, they can be prepared by dissolving the hydrogenate in the softened isomerate. However, it is preferred to heat the components to melting to speed solution. At the upper ranges of melting points of the isomorphous compositions of this invention they can be rapidly prepared by mixing the melts of the two components.

The Figure shows the variation of melting points with compositions. As can be seen there is a smooth increase in the melting points with increases in hydrogenate content.

The compositions having 5, 12.5 and 25% hydrogenate contents have been formulated into creams, lipsticks, lip balms, candles and fry-lubricants as replacements for the usually used waxes and performed as well or better as replacements therefore.

When molded into a lipstick, the compositions containing 12.5% hydrogenate retain good strength and do not soften appreciably in contact with body heat. No shattering or dis-figuration occurs when such lip-sticks in metal cases are subjected to standard 5-foot drop-tests to demonstrate brittleness.

Additionally, the stability of both components of the compositions and the compositions themselves to heat, light and oxidation, and general lack of toxicity makes the compositions of this invention particularly useful for cosmetics, and in foods. In cosmetics, the compositions replace waxes as in lipsticks and creams. They have excellent emollient qualities when properly formulated in creams. In lip-sticks they raise the melting points without embrittlement and yet do not interfere with the smoothness of application. The compositions are compatible with the oils, sterols, detergents and dyestuffs commonly used in cosmetics. The compositons also are useful as components in hair laquers, dressings and shampoos.

In the food industry, the compositions of this invention are particularly useful in lubricant compositions for food machinery, as replacements for bread-pan greases, and as fat free fry-pan lubricant sprays. In the latter uses the compositions of this invention are dissolved in a non-toxic, low boiling solvent, injected into an aerosol can and then a propellant is introduced. The solvent is usually ethanol and the propellant selected from among hydrocarbons, flurocarbons and carbox dioxide.

As can be seen from the Figure, the addition of as low as 5% of hydrogenate to the isomerate, results in a melting point elevation of 16° C. relative to the melting point of the isomerate.

As mentioned above, the present invention affords solid products from the semi-solid isomerate with additions of as little as 1% of hydrogenated jojoba oil.

Experiments A and B below provide comparisons of the qualities of the compositions of this invention for cosmetic and candle use as compared to mixtures of melts of the hydrogenate and jojoba oil.

EXPERIMENT A

Comparision of Mixes of (1) Jojoba oil and Hydrogenated Jojoba Oil, with (2) Jojoba Isomerate and Hydrogenated Jojoba Oil for Cosmetic and Lubricant Purposes.

1. Hydrogenated Jojoba Oil is mixed well with Jojoba Oil at concentrations of Hydrogenate in Oil of 2.5% to 75% at temperatures in excess of 70° C. when both materials are liquid. The resultant mixtures are allowed to cool to room temperature (25°C.) in jars (approximtely 1.0 inch in diameter and 0.5 inch high) and in cylinders (approximately 1.5 inches high and 0.375 inches in diameter). The resultant materials are examined for physical appearance, strength and consistency. In all cases the mixes are grainy in appearance and feel, with obvious bleeding of liquid oil occurring at all Hydrogenate concentrations (2.5% to 75%). The mixes at very low hydrogenate concentrations (2.5% to 25%) are slushy and at up to 50% exhibit poor strength on impact. Lipsticks made of mixes containing up to 25% hydrogenate concentrations tend to shatter or deform when dropped from heights of 5 feet in standard metal cases. Deformations occurs after short periods at body temperture (37°C.).

2. The experiment is repeated but this time using mixtures of hydrogenated jojoba oil and jojoba ismomerate. The resulting mixtures have a consistency and strength similar to commercially available waxes used for lip-sticks, lip balms, cosmetic creams and food equipment lubricants.

EXPERIMENT B

Comparison of mixes of (1) Jojoba Oil and Hydrogenated Jojoba Oil, with (2) Jojoba Isomerate and Hydrogenated Jojoba Oil for Candles 1. The experiment (A. 1) is repeated but at hydogenate concentrations up to 75% and the products are cast into candles approximately 5 inches long and ½ inch in diameter. In this range the products produced are not suitable for use as a candle material because of oil bleeding. At low hydrogenate concentrations, a grainy, low strength, slushy appearance manifests itself. At higher concentrations the product is hard and brittle with oil bleeding occurring. The candles do not burn evenly but sputter badly.

2. The experiment is repeated but using hydrogenate and the isomerate (31°C.). At hydrogenate concentrations ranging from 25% to 85% material suitable for candles is produced. The hardness and burning rates are uniform. No evidence of oil bleeding is found.

The examples which follow illustrate representative cosmetic and other formulations utilizing the compositions of this invention. The trademarked designation, Jojobutter, as used herein refers to the isomerate; isomorphous compositions containing same, including those according to this invention containing the isomerate and hydrogenate of jojoba oil in isomorphous mixture. The number following the trademark term jojobutter refers to the nominal melting, liquifying or softening point in degrees Celcius of the specific composition and indicates its "melting" grade.

The compositions according to this invention may replace or be combined with other waxes for specific properties. When the compositions are used to replace known hard waxes it is useful to substitute a melting grade that approximates the melting point of the wax being replaced.

The jojoba oil mentioned in the formulae is the natural refined cis-oil.

The basic cosmetic formulae, as herein modified, are from the Formulators Handbook published in 1980 by Amerchol Corp. and the trademarks mentioned herein are those of products of the publisher or are more specifically identified in said handbook as to source. The generic terms for the components therein used are those designated by the CFTA of approved and recognized products.

EXAMPLE 1—Lipstick

| | |
|---|---|
| Castor Oil | 49.0% |
| Acetulan | 4.0 |
| Beeswax | 9.0 |
| Jojobutter-31 | 10.0 |
| Isopropyl Palmitate | 11.0 |
| Ozokerite | 5.0 |
| Jojobutter 63 | 5.0 |
| Color and perfume | q.s. |

EXAMPLE 2—Sun Protection Lotion

| OIL PHASE | |
|---|---|
| Amerchol-101 | 4.2% |
| Mineral oil 70 wt. | 10.2 |
| Acetulan | 2.5 |

-continued

| OIL PHASE | |
|---|---|
| Isopropyl myristate | 8.5 |
| Glyceryl stearate | 4.2 |
| Laureth-23 | 4.2 |
| Jojoba oil | 0.5 |
| Jojobutter-51 | 2.5 |
| Amerscreen P | 3.0 |

| WATER PHASE | |
|---|---|
| Water | 40.8% |
| Polysorbate 20 | 1.7 |
| Carbomer 934, 3% slurry | 8.5 |
| Triethanolamine, 10% | 9.2 |
| Perfume and preservative | q.s. |

EXAMPLE 3—Sun Tan Oil

Vegetable oil based lotion. Good moisturizer.

| Amerscreen P | 3.0% |
|---|---|
| PPG-Myreth-3 | 30.0 |
| Acetulan | 5.0 |
| Amerchol-101 | 5.0 |
| Ameroxol OE-2 | 5.0 |
| Diisopropyl adipate | 1.0 |
| Octyl palmitate | 4.0 |
| Isodecyl oleate | 1.0 |
| Jojoba oil | 5.0 |
| Jojobutter-31 | 10.0 |
| Sesame oil | 31.0 |
| Perfume | q.s. |

EXAMPLE 4—Sun Protection Stick

Hard anhydrous butter with emollient properties.

| Amerscreen P | 1.5% |
|---|---|
| PPG-3-Myreth-3 | 5.0 |
| Acetulan | 3.0 |
| Amerchol CAB | 20.0 |
| Petrolatum | 20.0 |
| Cocoa butter | 10.0 |
| Modulan | 10.0 |
| Mineral oil | 10.0 |
| Jojoba oil | 6.0 |
| Olive oil | 6.0 |
| Sesame oil | 4.5 |
| Jojobutter-63 | 4.0 |
| Perfume | q.s. |

EXAMPLE 5—Sun Protection Cream

Soft butter with skin treatment properties.

| Amerscreen P | 1.5% |
|---|---|
| PPG-3-Myreth-3 | 5.0 |
| Acetulan | 3.0 |
| Modulan | 10.0 |
| Amerlate P | 3.0 |
| Jojoba oil | 7.0 |
| Sweet Almond oil | 7.0 |
| Jojobutter-51 | 10.0 |
| Microcrystalline wax | 3.0 |
| Mineral oil | 10.5 |
| Amerchol CAB | 20.0 |
| Petrolatum | 20.0 |
| Perfume | q.s. |

EXAMPLE 6—Soft Sun Cream

Soft butter suitable for tube dispensing with emollient properties and easy spreading.

| Amerscreen P | 1.5% |
|---|---|
| PPG-3-Myreth-3 | 5.0 |
| OHlan | 5.0 |
| Microcrystalline wax | 5.0 |
| Octyl palmitate | 8.5 |
| Jojobutter-31 | 10.0 |
| Microcrystalline wax | 15.0 |
| Amerchol-101 | 40.0 |
| Mineral oil | 10.0 |
| Perfume | q.s. |

EXAMPLE 7

Nongreasy cream. Designed to provide maximal sun protection.

| OIL PHASE: | |
|---|---|
| Jojoba oil | 7.0% |
| Amerchol CAB | 2.0 |
| Jojobutter-51 | 5.0 |
| Glyceryl stearate | 8.5 |
| Amerscreen P | 5.0 |
| Glucate | 1.0 |
| Glucamate SSE-20 | 1.0 |
| WATER PHASE: | |
| Water | 67.5 |
| Glucam E-10 | 2.0 |
| Triethanolamine | 1.0 |
| Perfume and preservative | q.s. |

EXAMPLE 8

Soft, elegant, nonionic cream, nongreasy. Excellent rub-in.

| Oil Phase | |
|---|---|
| Jojoba oil | 5.0% |
| Solulan PB-20 | 3.0 |
| Jojobutter-51 | 5.0 |
| Myristyl alcohol | 2.0 |
| OHlan | 1.0 |
| Glucate SS | 3.0 |
| Glucamate SSE-20 | 3.0 |
| Acetulan | 0.5 |
| Amerscreen P | 3.0 |
| Arlacel 165 | 5.0 |
| Amerchol L-101 | 10.0 |

| WATER PHASE | |
|---|---|
| Water | 58.0 |
| Glucam E-20 | 1.5 |
| Perfume and preservative | q.s. |

EXAMPLE 9—Candle Wax

| Jojobutter-63 | 80% |
|---|---|
| Microcrystalline Wax | 20 |

EXAMPLE 10—Candle Wax

| Jojobutter-63 | 90.0% |
|---|---|

| | |
|---|---|
| Polyethylene | 1.0 |
| Petrolatum | 9.0 |

EXAMPLE 11—Pan Release (aerosol)

| | |
|---|---|
| Jojobutter-51 | 10% |
| Ethanol | 90 |

The partial solution of the Jojobutter was introduced into an aerosol can. The pressurized propellant was then introduced to complete the solution. Applied as a spray to bake pans and fry pans, it provided excellent release of the baked goods from the bake pans and reduced adherence of residual foods to the fry pans.

EXAMPLE 12—Pan Releases (non-aerosol)

| | |
|---|---|
| Jojobutter-47 | 24% |
| Corn oil | 10 |
| Emulsifier (Food Grade) | 5 |
| Water | q.s. |

The emulsion is prepared in a homogenizer. The concentrate is bottled with directions for dilution. It is diluted wiht more water and sprayed unto the pan before frying or baking.

The invention claimed is:

1. A homogeneous compositon consisting essentially of trans-isomerized jojoba oil having a liquifying point of 25°–44° C. and hydrogenated jojoba oil in the isomorphous state of mutual solution.

2. The composition according to claim 1 wherein the isomorphous solution is in the solid state.

3. The composition according to claim 1 wherein said hydrogenate comprises five to ninety-five percent of said composition.

4. The composition according to claim 1 wherein the trans-isomerized jojoba oil component of said composition has a liquifying point in the range about 28°–35° C.

5. The composition according to claim 4 wherein said isomerized component has a liquifying point of about 31° C.

* * * * *